(12) United States Patent
Coifman (10) Patent No.: US 7,029,656 B2
(45) Date of Patent: Apr. 18, 2006

(54) METHODS AND FORMULATIONS FOR THE EFFICIENT DELIVERY OF WATER-INSOLUBLE DRUGS BY NEBULIZER

(76) Inventor: Robert E. Coifman, 1122 N. High St., Millville, NJ (US) 08332

( * ) Notice: Subject to any disclaimer, the term of this patent is extended or adjusted under 35 U.S.C. 154(b) by 0 days.

(21) Appl. No.: 10/168,120

(22) PCT Filed: Dec. 15, 2000

(86) PCT No.: PCT/US00/34304

§ 371 (c)(1),
(2), (4) Date: Oct. 7, 2002

(87) PCT Pub. No.: WO01/47491

PCT Pub. Date: Jul. 5, 2001

(65) Prior Publication Data

US 2003/0211046 A1 Nov. 13, 2003

Related U.S. Application Data

(60) Provisional application No. 60/171,997, filed on Dec. 23, 1999.

(51) Int. Cl.
*A61K 9/14* (2006.01)
*B05B 9/00* (2006.01)
*B05B 9/03* (2006.01)
*A61M 5/08* (2006.01)

(52) U.S. Cl. .......................... 424/43; 424/45; 424/46; 424/278.1; 424/489; 514/1; 514/826; 514/886; 514/937; 514/938; 514/943; 514/958; 514/959; 128/203.12; 128/203.15; 128/203.23; 128/203.24

(58) Field of Classification Search .................. 424/43, 424/46, 45, 489, 278.1; 514/1, 826, 886, 514/937, 938, 943, 958, 959; 128/203.12, 128/203.15, 203.23, 203.24
See application file for complete search history.

(56) References Cited

U.S. PATENT DOCUMENTS

| 3,641,078 A | 2/1972 | van der Kerk et al. .. 260/429.7 |
| 4,044,148 A | 8/1977 | Wright et al. ................ 424/317 |
| 4,963,367 A | 10/1990 | Ecanow ...................... 424/485 |
| 5,260,335 A | 11/1993 | Wagner et al. .............. 514/532 |
| 5,388,574 A * | 2/1995 | Ingebrethsen .......... 128/203.17 |
| 6,241,969 B1 * | 6/2001 | Saidi et al. .................... 424/45 |

FOREIGN PATENT DOCUMENTS

| EP | 0 100 964 A | | 2/1984 |
| EP | 0100964 | * | 2/1984 |
| EP | 0 351 720 | | 1/1990 |
| JP | WO 99/44594 | | 10/1999 |
| WO | WO 9917754 A1 * | | 4/1999 |

OTHER PUBLICATIONS de Benedictis et al., "Nebulized Flunisolide in Infants and Young Children With Asthma: A Pilot Study", Pediatric Pulmonology 1995 21:310-315.

Bianco et al., "Prevention of $PGF_{2\alpha}$ Induced Brochoconstriction by Disodium Cromoglycate in Asthmatic Patients", IRCS Medical Science:Biochemistry 1976 4 (4) :147 XP009031558.

Robertson et al., "Principles of surfctant replacement", Biochimica et Biophysica Acta 1998 346-3361 XP-002283158, 1998.

* cited by examiner

*Primary Examiner*—Frederick Krass
(74) *Attorney, Agent, or Firm*—Licata & Tyrrell P.C.

(57) ABSTRACT

Formulations, methods and devices for producing formulations and methods for nebulizer delivery of formulations of water-insoluble drugs are provided. Also Fig. 1a          Fig. 1b

METHODS AND FORMULATIONS FOR THE EFFICIENT DELIVERY OF WATER-INSOLUBLE DRUGS BY NEBULIZER

This patent application is the National Stage of International Application No. PCT/US00/34304, filed Dec. 15, 2000, which claims the benefit of priority to U.S. Provisional Application No. 60/171,997, filed Dec. 23, 1999.

BACKGROUND OF THE INVENTION

Asthma is a chronic inflammatory disorder of the airways in which inflammation contributes to hyper responsiveness to allergic and irritant stimuli, to airflow limitation, to a broad spectrum of respiratory symptoms, and to disease chronicity. Features of this inflammatory process include denudation of airway epithelium, edema, recruitment and activation of various types of migratory inflammatory cells, and increased basement membrane collagen deposition which is believed to be the cause of the chronic changes known as asthmatic airway remodeling.

Topically acting corticosteroids are the most potent and consistently effective long-term control medication for asthma. Their broad action on the inflammatory process may account for their efficacy as preventive therapy. Their clinical effects include reduction in severity of symptoms, improvement in peak expiratory flow rate and spirometry, diminished hyper responsiveness of airways, prevention of exacerbations, and possibly the prevention of airway wall remodeling. Further, there are data suggesting that earlier treatment with inhaled topically acting steroids, measured in years following diagnosis of asthma, results in better long term outcome and lower cumulative aggregate dose of steroids needed for optimal control.

Topically acting corticosteroids for asthma are generally administered as aerosolized droplets released into a spacer or holding chamber from a pressurized metered dose inhaler, and slowly inhaled from expiration or resting lung volume to maximum inspiratory volume by the patient, who then holds his breath for at least 10 seconds. Alternative devices are dry powder inhalers, activated by sucking from expiration or resting lung volume to maximal inspiration, followed by similar breath-holding.

The most widely favored delivery system for inhaled asthma medications for children who are too young to effectively use metered dose aerosols or dry powders, and for patients of any age whose airways are so irritable that they will cough out medications inhaled from metered dose or dry powder inhalers, is the compressor-driven jet nebulizer. This device generates a mist of droplets of medication in aqueous solution which is inhaled through either a mouthpiece or a mask. The market for this type of drug delivery system is large enough to have supported the development of inexpensive equipment for home use that is easy to use and reasonably efficient at delivering particles in the size range needed for effective topical treatment of asthma. The distribution system for this type of equipment makes it available at competitive prices throughout the United States. There are also other types of nebulizers designed for the same market, one being ultrasonic, in which mist is generated by a small plate vibrating at ultrasonic frequency instead of by turbulence created by a jet of compressed air. Some may become more popular in the future as ways to generate aerosols with different particle size distribution. It is anticipated that most will be designed to compete with the jet nebulizer market, for nebulization of liquids with nebulization characteristics approximating those of physiologic saline, and in volumes of 1 to 5 ml.

Topically acting corticosteroids are not sufficiently water-soluble to deliver effective treatment doses in practical volumes of nebulizable solution. This makes the most potent and consistently effective long-term control medications for asthma unavailable to young children, for whom early treatment with these medications offers the greatest potential for long term reduction in severity.

There have been previous attempts to overcome this problem.

Metered dose aerosol holding chambers have been designed with valves and masks, to be placed over a child's mouth and nose, so that droplets of medication sprayed into the chamber from an "adult" metered dose asthma inhaler will be inhaled in the course of either the child's normal breathing, or (as many young children resist the devices) the child's crying. Some parents, some physicians and some investigators find these devices convenient and effective, many find them much less so.

Unit doses of small, readily absorbable particles of water-insoluble, topically-acting steroids have been packaged with aqueous vehicles for nebulizer administration as aqueous suspensions. Such products have shelf life stability problems because of agglomeration of small drug particles into larger ones over time.

The recently published international PCT application WO 99/44594 discloses a drug delivery system in which water-insoluble drugs are prepared as lipid-water emulsions, freeze-dried, and dispersed in water for nebulization. Emulsions, like suspensions, are two-phase systems which, over time, undergo physical transition to lower energy states. Maintenance of a boundary between phases takes energy, so that a lower energy state can be achieved by reducing the surface area of this boundary. For a solid-in-liquid suspension the physical transition that takes place over time is particle agglomeration. For an emulsion, it is dissociation.

The present invention is an application of a model based on principles of physical chemistry, for the design of formulations of topically acting corticosteroids and other water-insoluble drugs for nebulizer inhalation in aqueous vehicles, which avoid the problems of particle agglomeration and dissociation of emulsions. The present invention also allows the economy of multiple dose packaging of concentrated drug in a state that is both ready-to-use and physically stable.

SUMMARY OF THE INVENTION

An object of the present invention is to provide formulations and procedures for preparing formulations using commercially marketed sterile saline, sterile buffered saline or other sterile aqueous diluents, as vehicles for the nebulizer delivery of water-insoluble drugs. In the present invention, a water-insoluble drug is dissolved in a non-aqueous solvent at a sufficiently high concentration that the volume of non-aqueous solvent per dose of drug is non-toxic. Such volumes are insufficient to operate presently available nebulizers. However, it has now been found that treatment doses in measured small volumes of these non-aqueous solutions can be mixed, immediately prior to nebulization, with larger volumes of aqueous vehicles. This results in formulations of sufficient volume to be administered effectively via commercially available nebulizers. These formulations exhibit characteristics of a two-phase liquid-liquid suspension. Dispersion of a small volume of the discontinuous, non-aqueous phase is maintained by the mixing action of the nebulizer in a large volume of continuous aqueous phase for the 10–20 minutes needed for administration of the treatment dose. The aqueous phase of the nebulizer formulation may also contain additional water-soluble drugs to be delivered to a patient concurrently with the water-insoluble drug dissolved in the non-aqueous phase of the suspension.

Another object of the present invention is to provide a method for improving delivery efficiency of any drug, water soluble or not, administered via non-continuous-flow jet nebulizer or ultrasonic nebulizer technology. This method involves "washing into the patient" with an extra aliquot of sterile diluent, most of the average of 40% of each dose left in present-day jet and ultrasonic nebulizers when the volume remaining in the device drops below the threshold needed for effective mist generation. This is done when the nebulizer stops generating mist, by adding additional sterile aqueous diluent to the nebulizer chamber, without additional drugs, restarting the nebulizer, and having the patient inhale the resulting aerosol until mist generation stops, again.

Another object of the present invention is to provide a device for quantitative measurement and dosing of sterile diluents such as buffered sterile saline from pressurized multi-dose, non-metered-dose canisters.

Yet another object of the present invention is to provide a device for clean, accurate and inexpensive measurement and dosing of small volumes of drugs in concentrated solution from multi-dose bottles.

BRIEF DESCRIPTION OF THE DRAWINGS

FIGS. 1a, 1b, and 1c show an embodiment of a measuring device for quantitative measurement and dosing of sterile diluents in preparation of formulations of the present invention. In this embodiment, the support of the device comprises two pieces, a trapezoidal rest, to support the tube at a selected angle and a triangular brace which provides structural support for the rest.

FIGS. 2a, 2b, and 2c show another embodiment of a measuring device for quantitative measurement and dosing of sterile diluents in preparation of formulations of the present invention. In this embodiment, the support of the device comprises two triangular wings upon which the tubular body rests and a trapezoidal bridge located between the wings for support.

DETAILED DESCRIPTION OF THE INVENTION

Water-insoluble drugs, such as topically acting asthma corticosteroids, are often sufficiently soluble in non-aqueous solvents such as, but not limited to, various glycols and/or alcohols alone or in combination, so that therapeutic doses can be in non-toxic solvent volumes of 0.05 to 0.5 ml. Such solutions are physically stable (i.e., they do not dissociate or agglomerate over the shelf life of the product) and they can be packaged inexpensively in multi-dose containers. They cannot be administered in this form with presently available nebulizers, however, because non-toxic volumes of their non-aqueous vehicles are insufficient for the operation of currently available nebulizers.

The present invention relates to new formulations comprising water-insoluble drugs and methods of delivering these formulations via nebulizer. In the present invention, single doses of water-insoluble drugs dissolved in small volumes of non-aqueous solution are mixed with larger volumes of aqueous vehicles just prior to nebulization. The aqueous vehicle may also contain water-soluble drugs to be administered concurrently with the water-insoluble drug. Accordingly, multiple prescribed inhaled medications can often be administered together using the formulations described herein.

What results is a formulation comprising a safe, small volume of non-aqueous vehicle containing water-insoluble drug, suspended in a sufficiently large volume of aqueous vehicle for effective delivery with proven, presently available nebulizer technology. While the exact molecular structure of the resulting mixture has not been determined, the physical behavior and/or characteristics of the mixture are that of a two-phase liquid-liquid suspension. By "nebulizer technology" it is meant to include both reliable and inexpensive jet nebulizers that are widely used at this time for delivery by inhalation of water-soluble drugs to infants and children with asthma, and improvements of the same or functionally comparable technologies such as ultrasonic nebulizers, to increase efficiency, alter drug deposition within the respiratory tract by varying particle size, and/or reduce treatment time.

The same principles of physical chemistry govern boundary behavior of all two-phase systems. Previously developed formulations for nebulizer administration of water-insoluble drugs in aqueous media involve the generation of a suspension prior to packaging. All such formulations will slowly dissociate and/or agglomerate during storage without the input of additional energy to maintain dispersion. With the present invention, however, a different outcome is achieved because of differences in both the timing of dispersion and the energy required to achieve and maintain dispersion.

In the present invention, the aqueous and non-aqueous components of the formulation are stored separately as stable one-phase solutions, and mixed immediately prior to nebulization. The energy required to achieve dispersion is sufficiently low when both aqueous and non-aqueous phases are low viscosity liquids, as in the formulations of the present invention, that dispersion can be created and maintained for what is usually a 10 to 20 minute duration of treatment, by the mixing action of the nebulizer used for administration of the drug.

It takes energy to maintain the boundary between the phases of a two-phase suspension. In the absence of an external source of this energy, every random molecular movement that reduces the total surface area of boundary between the two phases, will slightly disaggregate it, as the energy released by the reaction is dissipated into the environment as heat, and unavailable to energize molecular movement in the opposite direction. Accumulation of these spontaneous molecular movements over time results in particle agglomeration in solid particle suspensions, and in disaggregation of emulsions. Disaggregation does not occur with the formulation of the present invention because the aqueous and non-aqueous components are not mixed until the time of nebulization, and the energy needed to both create and maintain dispersion is provided by the operation of the nebulizer.

Examples of topically acting steroids for which this invention now makes possible the development of stable preparations for nebulizer use include, but are not limited to, beclomethasone, budesonide, flunisolide, fluticasone, mometasone and triamcinolone.

For the purposes of this invention, by "safe" it is meant a volume of non-aqueous solvent which is sufficiently small in quantity to pose either no significant risk of toxic effects, or a smaller risk of toxic effects than the alternative treatments the same patients would need in the absence of treatment using the present invention. As will be obvious to those of skill in the art upon this disclosure, the upper volume limit of "safe" may be different for different solvents and for infants and children of different ages. For any specific new drug application, the sponsor would have to satisfy the F.D.A. (or, for use in other countries, the appropriate regulatory office or administration) that the proposed volumes of the individual proposed solvent are in fact safe.

By "small" volume of non-aqueous solvent, it is meant a volume small enough not to perturb the nebulization characteristics of the mixture in comparison to the nebulization characteristics of the continuous aqueous phase if nebulized alone. "Small" is any volume that would become the discontinuous phase of what in the formulations of the present invention behaves as a two-phase liquid-liquid suspension which nebulizes with approximately the surface tension, droplet size, mist generation rate and other physical properties of the continuous, aqueous phase.

By "large" volume of aqueous phase, it is meant a volume large enough to operate the nebulizer. The device that is provided when a physician prescribes a compressor-driven nebulizer or a compressor-driven jet nebulizer for asthma, usually operates efficiently with a fill volume of up to 4 ml of a liquid with nebulization characteristics of physiologic saline. It stops generating mist, depending upon the model, when the body remaining in the chamber drops below 0.5 to 1.0 ml. Accordingly, for most present nebulizers, by large volume it is meant from about 2.5 to about 4 ml. Smaller operating volumes leave an unacceptably high percent of content in the chamber at the end of mist generation. Volumes much larger than about 4 ml do not allow enough room in presently available nebulizer chambers for effective mist generation. Since the physical properties of the aqueous phase are major determinants of the surface tension, droplet size, mist generation rate and other physical properties of formulations that behave as two-phase, liquid-liquid suspensions, the volume of this phase can be adjusted within the 2.5 to 4 ml range to optimize these properties.

The economy of packaging water insoluble-drugs as concentrated solutions in multi-dose containers is practical for the overwhelming majority of nebulizer applications, as the delivery systems in which they are used must be clean but not sterile. The equipment, after post-use cleaning, may be stored dry but not sterile. Aqueous diluents or vehicles used in large volume must be kept sterile; once opened, concentrated additives may be kept clean, but not necessarily sterile, with preservatives, as long as the quantities of preservatives needed to prevent microbial overgrowth, like the quantities of non-aqueous solvent needed to dissolve therapeutic doses of non-aqueous drugs for two-phase liquid-liquid suspension, are sufficiently small to be non-toxic and have no other adverse effects when diluted for nebulization. "Other adverse effects" would include impairment of nebulizer operation by sufficient concentrations of quaternary ammonium disinfectants which act as detergents to reduce surface tension, impair mist generation and thereby prolong treatment time. Most non-aqueous solvents have antimicrobial properties of their own, reducing the quantity of other preservatives needed for that purpose.

The present invention also relates to a method for improving delivery efficiency of any drug delivered via a nebulizer. Most present day nebulizers stop generating aerosol when the volume remaining in the chamber drops below approximately 1 ml. This is a significant fraction of a 2.5 ml dose of most unit dose medications marked for use with these devices. However, if the drug is packaged as a concentrate to be mixed with an aqueous diluent for delivery, when the nebulizer stops delivering aerosol and begins to sputter, indicating that the remaining volume has dropped below the threshold for effective operation, another dose of aqueous diluent can be added and nebulized into the patient, to wash in the majority of the remaining medication. With presently available nebulizers, volumes of 2.5 to 3.5 ml are optimal for this step. As will be obvious to those of skill in the art upon reading this disclosure, this method of minimizing drug wastage and improving drug delivery efficiency is also useful with nebulizable formulations other than those described herein.

The pharmaceutical industry is beginning to explore inhalation of nebulized dosage forms as a route of systemic delivery of various drugs for which there is not always effective and predictable oral absorption. Some are water-soluble, others are not. The formulations and methods of the present invention for drug delivery, as well as the methods for minimizing drug wastage upon delivery of a nebulized drug, are clearly applicable to delivery by nebulizer of such other drugs.

Dosing by mask to an infant or young child is effective but not quantitatively reproducible, because of variable loss of nebulized drug during expiration and variable deposition of each inspired "bolus" because of variable depth of inspiration and duration of breath-holding.

However, dosing by mouthpiece to an older child or adult, with a nebulizer chamber or compressor-chamber combination delivering a high and reproducible fraction of respirable particles and with a low residual volume at the end of aerosol generation, and a thumb valve to interrupt mist generation and prevent drug loss during breath-holding and expiration, is much more reproducibly quantitative. If drug is dosed into the nebulizer chamber in a volume of 3.5 ml, and residual volume of the nebulizer chamber is 0.5 or 1.0 ml (the lower value achievable with certain models of nebulizer chamber), the fraction of drug left in the nebulizer at the end of treatment will be 14.3 or 28.6%. Washing in this left-over drug with 3 ml of sterile or buffered sterile saline in accordance with the method described herein will reduce drug wastage to 2.4% or 9.5%. Accordingly, using the formulations and methods of the present invention it is now feasible for developers of both respiratory and non-respiratory drugs to quantitatively deliver drugs by inhalation to older children and adults using economical and reliable nebulizer systems that are already available.

The developer of a specific drug application has various options in using the formulations and methods of this invention.

For example, in one embodiment, a water-insoluble drug can be mixed with either a unit dose formulation of a water-soluble drug in aqueous diluent prescribed for concurrent administration, or with a commercially available sterile saline or buffered sterile saline diluent, with or without addition of a concentrated, small volume of any other water-soluble drug also prescribed for concurrent administration. In this embodiment, it is preferred that any remaining drug or drugs in the nebulizer chamber be washed in via an additional aliquot of commercially available sterile saline or buffered sterile saline diluent.

In another embodiment, for a water-soluble drug, the drug can be supplied as a concentrate for dilution with a commercially available sterile saline or buffered sterile saline diluent, or as a pre-packaged unit dose. In this embodiment, it is also preferred that any remaining drug in the nebulizer chamber be washed in via an additional aliquot of commercially available sterile saline or buffered sterile saline diluent.

Commercially available formulations of sterile saline or buffered sterile saline include: individually sealed 3 ml unit dose ampules with a present cost to the user of approximately $0.30/ampule ($0.10 per ml); 8 ounce pressurized metered dose, multi-dose canisters of sterile saline manufactured as a nebulizer diluting solution, dispensing 1 ml each time it is pressed, at a cost of approximately $0.042 per ml; and 12 ounce pressurized non-metered dose, multi-dose canisters of borate-buffered sterile saline sold as a cleaning solution for contact lenses, which ranges in cost from approximately $0.009 to $0.015 per ml.

A manufacture of formulations of the present invention can achieve the greatest reduction in combined insurer plus user cost, without reducing its own revenues per dose sold, by obtaining FDA certification of its drug for use with the least expensive formulation of sterile saline or buffered sterile saline diluent. Currently, 12 ounce pressurized non-metered dose, multi-dose canisters of buffered sterile saline marketed as a cleaning solution for contact lenses are the least expensive formulations. The manufacturer of a drug using this product as a diluent can package each multi-dose bottle of concentrated solution of drug with a quantitative measuring device and instructions for its use with pressurized, non-metered-dose, multi-dose canisters of sterile saline.

The design features of a quantitative measuring device useful in the present invention can be best understood as features to implement the following performance specification. The device shall quickly, accurately and reproducibly measure and dispense into a nebulizer chamber a pre-determined (i.e. not user adjustable) volume in the several milliliter range of a physiologic saline or buffered saline solution that has just been released from a pressurized canister. Since the saline will contain effervescing bubbles of trapped propellant as it is dispensed into the device, the device must accommodate the volume of bubbles and allow them to dissipate without affecting the accuracy of the volume it then dispenses.

Figure 1A:
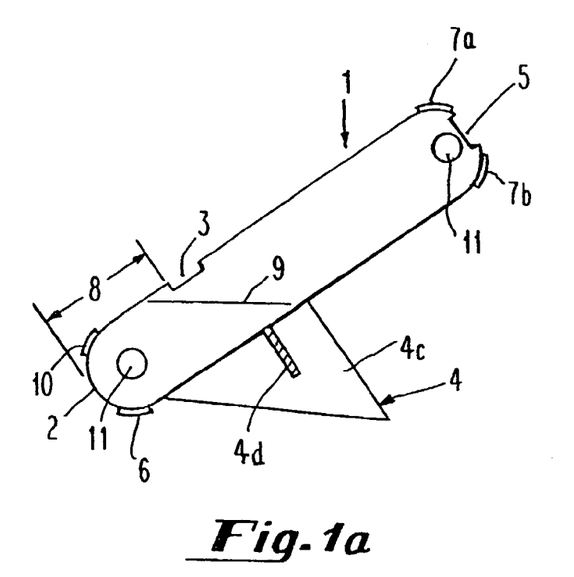
FIG. 1a provides a side view diagram of the tubular body in its resting position in the support.
Figure 1B:
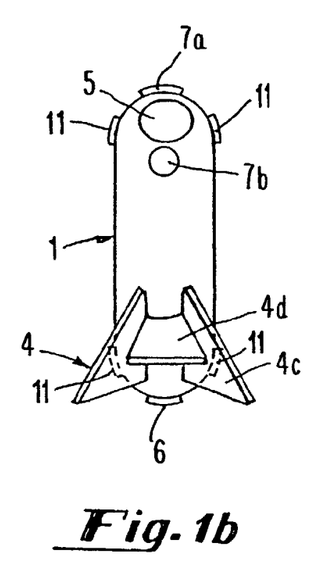
FIG. 1b provides an end-view diagram of the measuring device in the same position.
Figure 1C:
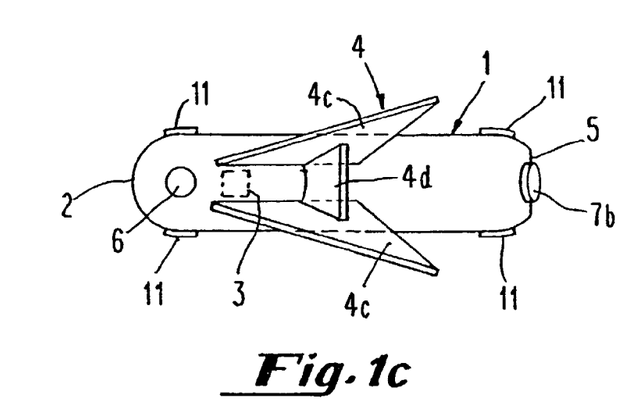
FIG. 1c provides a bottom view of this device.
Figure 2A:
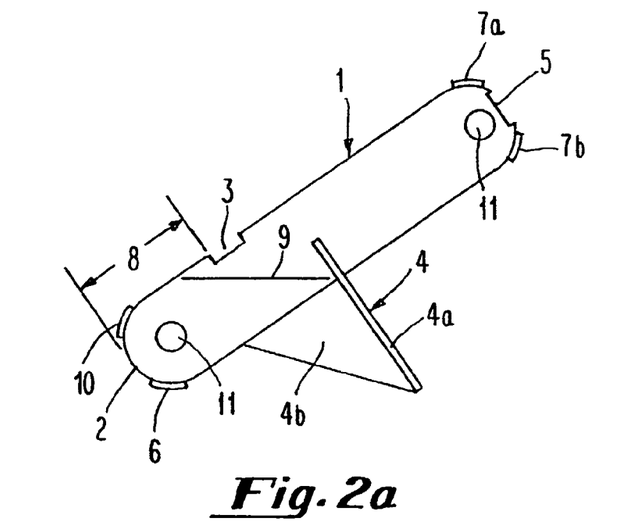
FIG. 2a provides a side view diagram of the tubular body in its resting position in the support.
Figure 2B:
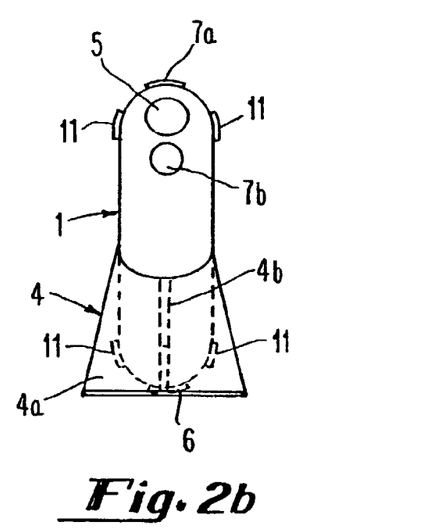
FIG. 2b provides an end-view diagram of the measuring device in the same position.
Figure 2C:
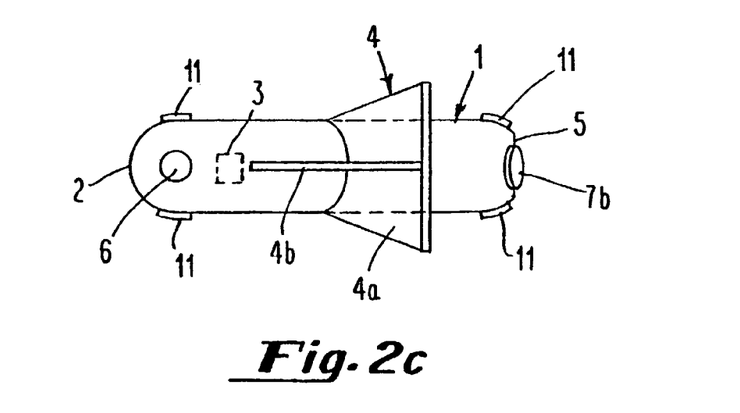
FIG. 2c provides a view from the bottom, perpendicular to the long excess of the tubular portion of the device.

Representative embodiments of a quantitative measuring device for use in preparing formulations of the present invention are depicted in FIGS. 1a, 1b and 1c and in FIGS. 2a, 2b and 2c. In simplest form, the measuring device comprises a tubular body 1, preferably cylindrical in shape as this geometry is easy to keep clean and is less favorable for trapping of bubbles as compared to polygonal shapes. The bottom of the tube 2 is closed and is preferably hemispherical in shape, again for ease in cleaning and to prevent trapping of bubble in corners. The top of the tube 5 is open. In one embodiment of the invention, the top of the tube 5 is tapered inward, in similar fashion to the top of a jar, to minimize spills when the device is tapped to dislodge bubbles. In another embodiment, the tubular body of the device 1 is minimally conical, increasing in diameter from bottom to top by up to 1 to 2% per unit length. This design should allow a less expensive fabrication process. The reduced spill tendency achieved by a narrowed neck in the first embodiment is achieved in this embodiment by increasing its length. The following support designs or any other support shape that meets the performance specifications described herein can be used in both of these embodiments.

A support 4 is molded into the tubular body 1 to hold the tube at a convenient angle to allow bubbles of propellant in the diluent to effervesce without displacing volume to be measured from the tube. In one embodiment, as depicted in FIGS. 1a, 1b, and 1c, the support 4 comprises two pieces, 4a and 4b which form a trapezoidal rest 4a which supports the tube at a selected angle, and a triangular brace 4b which provides structural support for the rest. In another embodiment, as depicted in FIGS. 2a, 2b and 2c, the support 4 comprises two triangular wings 4c and a trapezoidal bridge 4d located between the wings for support. In both embodiments, a proturbance 6 is placed on the outer surface of the hemispherical bottom 2 of the tubular body 1. This proturbance 6 provides a resting point for the device when placed on a flat surface at an angle against the support. The tubular body 1 also comprises a square hole 3 with sides parallel and perpendicular to the long axis of the tubular body 1 and centered on the side of the tube which is pointed up when the device is rested on its support 4. The hole 3 is sized and positioned so that when the device is filled with slightly more diluent than a desired dose and positioned vertically, the level of diluent will be above the bottom of the hole 3. In a preferred embodiment, the device further comprises proturbances, 7a and 7b, on the outer surface at the top of the tubular body, and proturbance 10 on the outer surface at the bottom of the tubular body to facilitate gripping the device with the thumb below proturbance 7a and the middle finger below proturbance 7b, to expel extra diluent through the hole 3 by gentle tapping. The distance 8 from the bottom 2 of the tubular body 1 to the bottom of the hole 3 is fixed so that the device will deliver the desired volume of diluent when used as described herein. The device may further comprise an optional fill line 9 on the outer surface of the tubular body 1 which provides a guide to slightly overfill the tubular body 1 from a non-metered, dose-pressurized canister, to allow for effervescence and subsequent delivery of an accurate dose, with minimal wastage. The device may optionally further comprise additional proturbances 11, located on the outer surface of the tubular body 1 at the top 5 and bottom 2 which serve as finger grips to grasp the device when rocking it on its support 4, to let it gently bounce on proturbance 6 to dislodge any bubbles that may adhere to the inner surface after completion of effervescence. Users may alternatively press down on proturbance 7a to rock the device on its support and let it fall back, to dislodge any bubbles.

To use this device, sterile saline or sterile buffered saline diluent is dispensed into the device from the non-metered, dose-pressurized canister in which it is supplied. The device is tipped to its desired fill angle as it is filled, to keep its contents from spilling out through hole 3. The device is filled to the fill line 9, and placed on a flat surface to allow effervescing bubbles to rise to the surface of the liquid in the device. Any bubbles that may have adhered to the inner surface of the device can be dislodged by tilting the device onto its support and letting it fall back, so that the proturbance 6 falls against the surface on which the device rests thereby jarring the bubbles loose. The device is then picked up, held over the sink, rotated to a vertical position, and proturbance 10 is gently tapped against the inside wall of the sink to jostle diluent in excess of the desired fill level out of hole 3. Proturbances 7a and 7b are incorporated into this invention to reduce the risk of the device slipping out of the user's hand, when it is tapped against the inner side wall of a sink to expel excess liquid. The remaining content of the device is then poured into the nebulizer chamber, either before or after other medications are added or as a chaser after the nebulizer has stopped generating mist.

If the geometry of a nebulizer is such that the support of the measuring device gets in the way of pouring from the measuring device into the chamber, the diluent may first be poured into a medicine cup and then into the nebulizer chamber. Accordingly, a manufacturer wishing to minimize the possibility of having the protruding support of the diluent dose-measuring device interfere with pouring into certain models of nebulizer chambers may also supply a small plastic medicine cup together with the device, with a multi-dose bottle of the drug.

The measuring device of the present invention is designed so that the volume of diluent or chaser in the measuring device, which is then poured into the receptacle, is accurate and reproducible, independent of the initial volume of overfill and independent of tapping pressure and technique.

The manufacturer of drugs for nebulizer formulation which are provided in multi-dose bottles containing a concentrated solution of drug can also include a dosing device to facilitate the clean, inexpensive and accurate measurement and dosing of small volumes of concentrated drug solution from the multi-dose bottle, into the nebulizer chamber for mixing with large volumes of aqueous media to form the two-phase liquid-liquid suspension. The performance specification for this device is that it be able to accurately measure and dispense volumes from 0.05 to 0.5 ml, drawn from a multi-dose bottle, that is be as easy to keep clean as the graduated plastic dropper tips presently supplied with concentrated aqueous multi-dose nebulizer formulations for which dose volumes range from 0.25 to 0.5 ml, and that it be inexpensive to manufacture and distribute. The same device may be used for accurate dosing of similarly small volumes of water soluble drugs in aqueous media, extending downward from about 0.25 ml to 0.05 ml the range of clean, inexpensive and accurate measurement of small volumes of all drugs for nebulizer administration.

This device of the present invention comprises a screw-on cap for a multi-dose medicine bottle, either incorporating a gasket or with an open top and holding in place a gasket with a flexible seal, impermeable to its liquid contents and preferably transparent, to fit around the shaft of a mass-produced, plastic 0.5 ml medicine syringe so that the syringe can slide in and out of the bottle. The syringe is similar to those manufactured for individuals with diabetes to self-inject insulin, except that for this use it will be provided either with no needle or with a relatively large bore, blunt tip needle.

Figure 3:
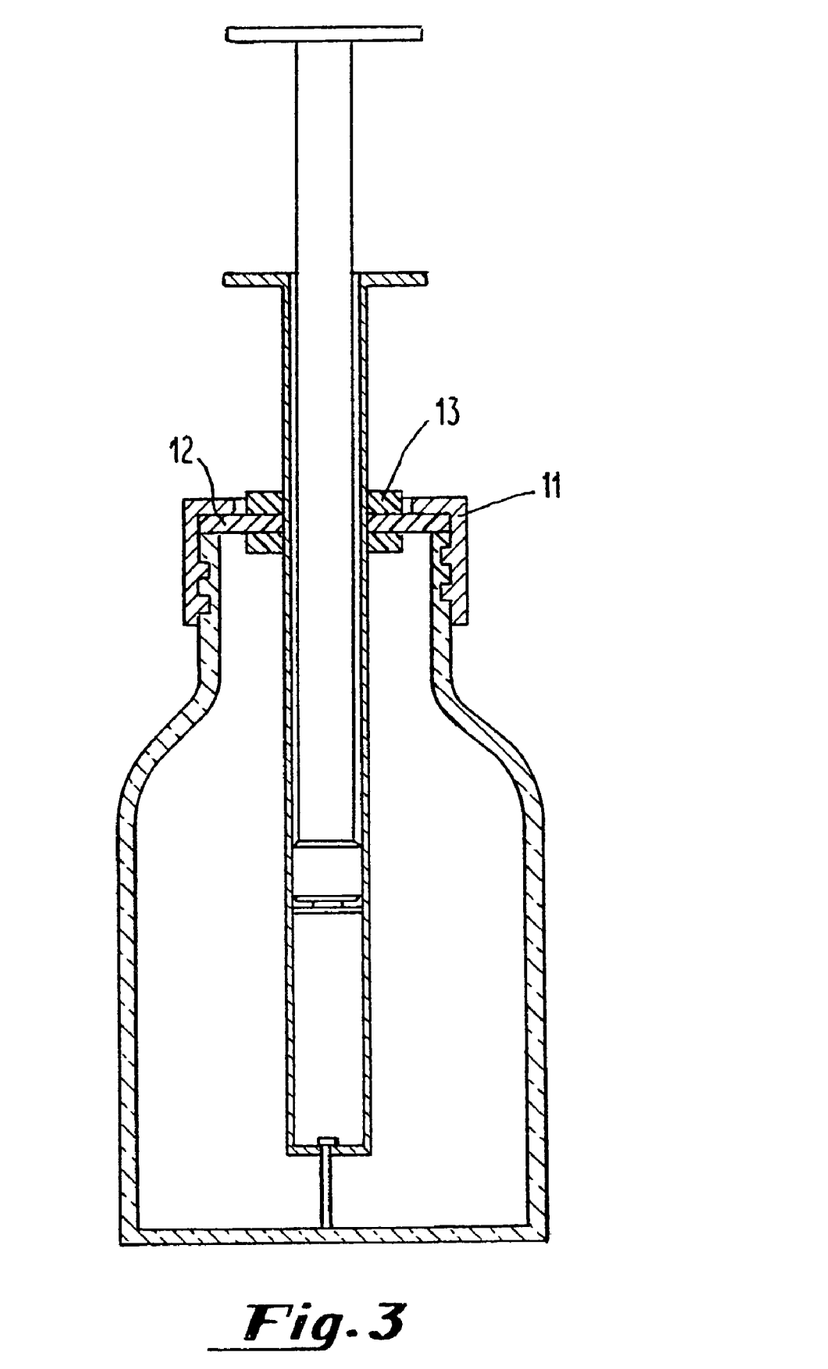
FIG. 3 provides a cross-sectional side view of a device to facilitate measuring and dosing small volumes, i.e. 0.05 to 0.5 ml, of non-water-soluble drugs from a multi-dose bottle for nebulizer formulation in a clean, inexpensive and accurate manner.

The device, as depicted in FIG. 3, comprises the components and elements described above. Namely, this device comprises a screw-on cap 11, a gasket 12 fitted into the top of the screw-on cap; and a liquid tight seal 13 which fits around the shaft of a plastic syringe, allowing the syringe to slide in and out of the bottle. It combines the cleanliness in repeated use of an ordinary medicine dropper top, which need never be put down anywhere but inside its clean bottle, the accuracy of a syringe, and the economy of using a product that is already mass produced for a very large market.

Different plastic syringes may be made with silicone lubricants of different composition, or with no lubricant at all. In selecting a syringe for this use with non-aqueous media, a drug manufacturer will have to ensure that syringe lubricant is not dissolved by the non-aqueous medium employed, making the syringe stick and exposing the patient to inhalation of lubricant.

EXAMPLE

A solution of flunisolide dissolved in a mixture of propylene and polyethylene glycol is marketed for topical use as a nose spray in allergic rhinitis. This solution may be administered by nebulizer as the small volume, non-aqueous phase of what behaves as a two-phase liquid-liquid suspension in aqueous media, as described herein.

This formulation of flunisolide has been demonstrated to offer young children the benefit of effective nebulized topical steroid therapy for asthma for the first time. In doses of 50 to 100 μg given up to 4 times per day, this formulation has proven convenient, effective and free of apparent adverse effects in the treatment of multiple patients, many over relatively long term treatment intervals. Both physician and parents have observed improved control of asthma, reduced need for acute care, reduced need for oral steroids, and reduced need for hospital and emergency department care in more than one hundred patients treated with this formulation of the present invention.

For these patients, a measured volume, typically 0.25 to 0.5 ml, of flunisolide dissolved in a mixed glycol non-aqueous phase was mixed with 2.5 to 3.5 ml of aqueous phase consisting of a physiologic or buffered physiologic saline solution or a unit dose formulation of a co-administered water-soluble drug in aqueous solution, with or without other water-soluble drugs added as measured volumes of multi-dose aqueous formulations.

When the nebulizer began to sputter, indicating insufficient remaining volume for effective aerosol generation, the parent or patient was instructed to add an additional 2.5 to 3.5 ml of sterile saline or sterile buffered saline, from a pressurized, multi-dose container.

Patients in the treatment group reported in this example generally had insurance coverage for medications, but had to purchase diluent out-of-pocket. With an average treatment frequency for the more than 100 patients of two treatments per day for an average treatment interval greater than one year, the availability of sterile buffered saline diluent at a cost of approximately $0.01 per ml, dosed with a slightly less precise measuring device than that described herein, was a major enhancer of compliance with prescribed treatment.

What is claimed is:

1. A nebulizer device, wherein said device contains a formulation for administration of a water-insoluble drug via the nebulizer consisting essentially of:
   (a) a entail volume of a solution of water-insoluble drug dissolved in a nonaqneous solvent, said small volume of solution not perturbing nebulization characteristics of a mixture of aqueous media and the small volume of solution in comparison to nebulization characteristics of the aqueous media if nebulized alone; and
   (b) a large volume of aqueous media, said large volume of aqueous media being large enough to operate the nebulizer; wherein, prior to administration, said small volume of solution has been mixed with said large volume of aqueous media to form a mixture that behaves as a two-phase liquid-liquid suspension in which dispersion of the solution in the aqueous media is maintained by mixing action of the nebulizer.

2. The nebulizer device of claim 1 wherein the aqueous media of the formulation comprises a water-soluble drug to be administered concurrently with the water-insoluble drug.

3. A method for delivery of a water-insoluble drug via a nebulizer to a patient consisting essentially of:
   (a) dissolving a water-insoluble drug in a small volume of nonaqutous solvent to form a drug solution, said small volume of nonaqueous solvent not perturbing nebulization characteristics of a mixture of aqueous media and the small volume of nonagusous solvent in comparison to nebulization characteristics of the aqueous media if nebulized alone;
   (b) mixing the drug solution with a large volume of aqueous media to form a mixture that behaves as a two-phase liquid-liquid suspension, said large volume of aqueous media being large enough to operate the nebulizer; and
   (c) delivering this mixture to the patient via the nebulizer with mixing action, the driving energy of which both creates and maintains dispersion of the drug solution in the aqueous media during the period of drug delivery by inhalation.

4. The method of claim 3 wherein the aqueous media comprises a solution of one or more water-soluble drugs to be administered concurrently with the water-insoluble drug.

5. A method for delivery of a water-insoluble drug via a nebulizer to a patient consisting essentially of:
   (a) dissolving a water-insoluble drug in a small volume of nonaqueous solvent to form a drug solution, said small volume of nonaqusous solvent not perturbing nebulization characteristics of a mixture of aqueous media and the small volume of nonaqueous solvent in comparison to nebulization characteristics of the aqueous media if nebulized alone;
   (b) mixing the drug solution with a large volume of aqueous media to form a mixture that behaves as a two-phase liquid-liquid suspension, said large volume of aqueous media being large enough to operate the nebulizer;
   (c) delivering this mixture to the patient via the nebulizer with mixing action, the driving energy of which both creates and maintains dispersion: of the drug solution in the aqueous media during the period of drug delivery by inhalation; and
   (d) adding an aliquot of sterile saline or sterile buffered saline to a nebulizer chamber after delivering the drug mixture to the patient to further mix with any remaining drug in the nebulizer chamber and nebulizing the remaining drug mixture into the patient.

6. A nebulizer device, wherein said device contains a formulation for administration of a drug via the nebulizer, the formulation consisting essentially of a small volume of a solution of a drug requiring dilution prior to administration, said small volume of solution of drug not perturbing nebulization characteristics of a mixture of aqueous vehicle and the small volume of solution of drug in comparison to nebulization characteristics of the aqueous vehicle if nebulized alone, and a large volume of aqueous vehicle, said large volume of aqueous vehicle being large enough to operate the nebulizer; wherein, prior to administration, said small volume of solution of drug requiring dilution prior to administration has been mixed with said large volume of aqueous vehicle to form a that behaves as a two-phase liquid-liquid suspenion suitable for administration via the nebulizer.

* * * * *

UNITED STATES PATENT AND TRADEMARK OFFICE
CERTIFICATE OF CORRECTION

| | | |
|---|---|---|
| PATENT NO. | : 7,029,656 B2 | Page 1 of 1 |
| APPLICATION NO. | : 10/168120 | |
| DATED | : April 18, 2006 | |
| INVENTOR(S) | : Robert E. Coifman | |

It is certified that error appears in the above-identified patent and that said Letters Patent is hereby corrected as shown below:

At column 9, line 33, please delete "be".

At column 10, line 54, please delete "entail" and insert --small--.

Signed and Sealed this

First Day of April, 2008

JON W. DUDAS
*Director of the United States Patent and Trademark Office*